US011247160B2

(12) United States Patent
Chen et al.

(10) Patent No.: US 11,247,160 B2
(45) Date of Patent: Feb. 15, 2022

(54) AIR PURIFIER HOUSING

(71) Applicant: Airplove (Xiamen) Electronic Co., Ltd., Fujian (CN)

(72) Inventors: Jueyuan Chen, Fujian (CN); Zhangcan Lin, Fujian (CN); Jinbo Xu, Fujian (CN); Tingping Lei, Fujian (CN)

(73) Assignee: AIRPLOVE (XIAMEN) ELECTRONIC CO., LTD., Fujian (CN)

( * ) Notice: Subject to any disclaimer, the term of this patent is extended or adjusted under 35 U.S.C. 154(b) by 310 days.

(21) Appl. No.: 16/503,895

(22) Filed: Jul. 5, 2019

(65) Prior Publication Data

US 2020/0101409 A1  Apr. 2, 2020

(30) Foreign Application Priority Data

Sep. 28, 2018  (CN) .......................... 201821589872.6
Jun. 4, 2019   (CN) .......................... 201920831097.9

(51) Int. Cl.
| | |
|---|---|
| *B01D 46/00* | (2006.01) |
| *F16H 21/44* | (2006.01) |
| *B01D 46/42* | (2006.01) |
| *A61L 9/16* | (2006.01) |

(52) U.S. Cl.
CPC ..... *B01D 46/0005* (2013.01); *B01D 46/4227* (2013.01); *F16H 21/44* (2013.01); *A61L 9/16* (2013.01); *A61L 2209/14* (2013.01)

(58) Field of Classification Search
CPC . B01D 46/0005; B01D 46/4227; F16H 21/44; A61L 9/16; A61L 2209/14; F16M 11/123

USPC ................................ 55/471, 490–579, 385.1
See application file for complete search history.

(56) References Cited

U.S. PATENT DOCUMENTS

| | | | |
|---|---|---|---|
| 2007/0261375 A1* | 11/2007 | Paterson ............ | B01D 46/0005 55/471 |
| 2017/0248153 A1* | 8/2017 | Park ...................... | F04D 29/703 |
| 2019/0226695 A1* | 7/2019 | Kim .......................... | F24F 6/16 |

FOREIGN PATENT DOCUMENTS

KR  20170010293 A * 1/2017 .............. F24F 1/005

* cited by examiner

*Primary Examiner* — T. Bennett McKenzie
*Assistant Examiner* — Qianping He
(74) *Attorney, Agent, or Firm* — Muncy, Geissler, Olds & Lowe, P.C.

(57) ABSTRACT

An air purifier housing comprises an outer cover and a bottom bracket with a center cavity which is open downwards and insertion grooves, recessing openings stretching into the center cavity are formed in side walls of the insertion grooves, insertion rods are fixed on the outer cover, which is inserted into the insertion grooves through the insertion rods; installation grooves corresponding to the recessing openings are in the insertion rods; and a limiting structure is in the center cavity and comprises a driving part and inner container protrusions which correspond to the recessing openings, and the driving part connects with the inner container protrusions and drives them to reach a first position where the inner container protrusions stretch out of the insertion grooves to be inserted into the installation grooves of the insertion rods or to reach a second position where the inner container protrusions retreat into the center cavity.

20 Claims, 15 Drawing Sheets

AIR PURIFIER HOUSING

BACKGROUND OF THE INVENTION

1. Technical Field

The invention relates to the technical field of air purifiers, in particular to an air purifier housing.

2. Description of Related Art

In recent years, the frequent occurrence of hazy and dusty air leads to the deterioration of urban air quality in China. As is known to all, certain dust particles, bacteria and viruses in air are harmful to human bodies, poisonous and harmful gases will be released within a certain time after home decoration, and harmful bacteria and viruses spreading in densely-populated public places may also do harm to public health. With the improvement of living standards, people are paying more and more attention to the living environment around and particularly to the indoor air quality, and various air purifiers are adopted to improve the indoor air quality so as to meet the higher and higher requirements for the surrounding air quality and the indoor air quality. As a result, a large number of air purifiers are developed to purify indoor air. However, the filter element in existing air purifier housings is difficult to replace.

BRIEF SUMMARY OF THE INVENTION

The objective of the invention is to solve the technical problem of complex replacement of the filter element in existing air purifier housings.

The technical solution adopted by the invention to fulfill the above objective is as follows:

An air purifier housing comprises an outer cover and a bottom bracket, wherein a center cavity which is open downwards is formed in the bottom bracket, insertion grooves are formed in the bottom bracket, recessing openings stretching into the center cavity are formed in side walls of the insertion grooves, insertion rods are fixedly arranged on the outer cover, the outer cover is inserted into the insertion grooves of the bottom bracket through the insertion rods, and installation grooves corresponding to the recessing openings are formed in the insertion rods; and a limiting structure is arranged in the center cavity of the bottom bracket and comprises a driving part and inner container protrusions, the inner container protrusions correspond to the recessing openings, and the driving part is connected with the inner container protrusions and drives the inner container protrusions to reach a first position where the inner container protrusions stretch out of the insertion grooves to be inserted into the installation grooves of the insertion rods or to reach a second position where the inner container protrusions retreat into the center cavity.

Furthermore, the driving part of the limiting structure is a rotary convex platform, at least one installation part extending inwards is formed on the inner wall of the center cavity, and the rotary convex platform is adaptively and rotatably arranged in the center cavity and is provided with recessing regions allowing the installation parts to be recessed therein and having a recessing area larger than the area of the installation parts; an L-shaped groove having a first end stretching to the top of the bottom bracket and a second end stretching into the center cavity is formed in each installation part, and the L-shaped grooves serve as the insertion grooves; the second ends of the L-shaped grooves are formed with the recessing openings and stretch into the center cavity, the inner container protrusions are rotary inner container protrusions, the recessing regions of the rotary convex platform extend towards the second ends of the L-shaped grooves to stretch out of the rotary inner container protrusions, and the insertion rods are adaptively inserted into the first ends of the L-shaped grooves; when the rotary convex platform is driven to rotate, the rotary inner container protrusions enter the installation grooves via the second ends of the L-shaped grooves, inner walls of the recessing regions are gradually attached to inner walls of the installation parts to realize limiting in a rotation direction; stop blocks are formed on the inner wall of the center cavity of the bottom bracket, engaging points formed on the periphery of the rotary convex platform, and either the stop blocks or the engaging points are convex arc pieces; and when the recessing regions are attached to the installation parts to realize limiting in the rotation direction, the stop blocks prevent the engaging points from moving in a direction opposite to the rotation direction so as to ensure limiting.

When a filter element needs to be replaced, the rotary convex platform is rotated in a reverse direction, the engaging points retreat to be separated from the stop blocks, the rotary inner container protrusions disengage from the installation grooves and the L-shaped grooves at the same time, at this moment, the outer cover can be detached from the bottom bracket with a small upward force, then the filter element to be replaced is taken out of the center cavity, and a new filter element is placed on the upper surface of the bottom bracket; afterwards, the outer cover is assembled (namely, the insertion rods are inserted into the L-shaped grooves), a rotary inner container is rotated in a forward direction, the rotary inner container protrusions enter the installation grooves via the L-shaped grooves, the engaging points stretch in the forward direction to be attached to the stop blocks, and the engaging points cannot retreat to be separated from the stop blocks in the absence of an external force, so that full locking is realized.

Furthermore, the number of the insertion rods, the L-shaped grooves, the installation parts and the recessing regions is greater than one, and the installation parts are arranged at intervals around the center of the center cavity.

Furthermore, either the stop blocks or the engaging points are semicircular, and the other ones are in a long strip shape; and the number of the stop blocks is consistent with that of the installation parts, and each stop block is arranged between two installation parts.

Furthermore, the air purifier housing further comprises a drive knob which is fixedly arranged on the periphery of the rotary convex platform and stretches out of the bottom bracket, and a first recessing hole allowing the drive knob to be recessed therein is formed in the bottom bracket.

Furthermore, the first recessing hole is in an inverted-L shape, and the drive knob is fixedly connected to the periphery of the rotary convex platform through a connector capable of adaptively moving in the first recessing hole.

Furthermore, the air purifier housing further comprises a base fixedly arranged in the center cavity of the bottom bracket, and the bottom of the base is adaptively flush with and attached to an opening of the center cavity of the bottom bracket.

Furthermore, locking pieces extending upwards are arranged on the base, second recessing holes allowing the locking pieces to be recessed therein are formed in the rotary convex platform, and third recessing holes allowing the locking pieces to be recessed therein are formed in the bottom bracket.

Furthermore, the number of the locking pieces is at least two, and the locking pieces are arranged at intervals around the center of the base.

Furthermore, the second recessing holes are long strip-shaped holes.

Furthermore, a circular blind hole which is open downwards is formed in the center of the bottom bracket, and the blind hole serves as the center cavity; and a positioning block extending downwards is formed at the center of the inner wall of the upper end of the center cavity, and a positioning hole allowing the positioning block to be adaptively inserted therein is formed in the center of the rotary convex platform.

Furthermore, the limiting structure further comprises swing arms which are pivoted to first stationary shafts in the center cavity, the inner container protrusions are connected with the swing arms and correspond to the recessing openings, the driving part is connected with the swing arms and drives the swing arms to swing back and forth, and the swing arms drive the inner container protrusions to reach the first position where the inner container protrusions stretch out of the insertion grooves to be inserted into the installation grooves of the insertion rods or to reach the second position where the inner container protrusions retreat into the center cavity.

Furthermore, the driving part comprises connecting rods, elastic pieces and a pin, wherein the middles of the swing arms are pivoted to the first stationary shafts in the center cavity, first ends of the swing arms are connected with the inner container protrusions, second ends of the swing arms are pivoted to first ends of the connecting rods, and the elastic pieces always apply a force towards second ends of the connecting rods to the connecting rods, so as to drive the connecting rods to move towards the second ends; the pin is movably inserted to abut against the second ends of the connecting rods and drives the connecting rods to overcome the force from the elastic pieces to move towards the first ends; and when the connecting rods move back and forth towards the first ends and the second ends, the swing arms are driven to swing back and forth, and then the inner container protrusions are driven to reach the first position or the second position.

Furthermore, the driving part further comprises a toggle rod, wherein the middle of the toggle rod is pivoted to a second stationary shaft in the center cavity, a first end of the toggle rod is connected with the pin, and a second end of the toggle rod extends out of the bottom bracket to form a toggle button.

Furthermore, the driving part further comprises an elastic base plate, wherein the elastic base plate covers a bottom opening of the center cavity of the bottom bracket and is fixedly connected with the pin, and the elastic base plate can be elastically pressed towards the interior of the center cavity to drive the pin to be movably inserted.

Furthermore, the air purifier housing further comprises a bottom cover, wherein the bottom cover is fixedly arranged in the bottom opening of the center cavity of the bottom bracket in a covering manner; and a through hole allowing the pin to be recessed therein is formed in the center of the bottom cover, and the bottom cover is concaved towards the interior of the center cavity to form a concave region allowing the elastic base plate to be elastically pressed therein.

Furthermore, the elastic pieces are tension springs, a stationary connecting column is arranged in the center cavity, the pin is of a hollow structure and is disposed around the stationary connecting column, first ends of the tension springs are fixedly connected to the stationary connecting column, second ends of the tension springs are fixedly connected to the second ends of the connecting rods, and recessing notches allowing the tension springs to be recessed therein are formed in the pin.

Furthermore, arc-shaped abutting parts matched with the outer wall of the pin are formed at the second ends of the connecting rods.

Furthermore, the number of the insertion grooves is more than one; the limiting structure is provided with a plurality of cooperative structures of the elastic pieces, the connecting rods and the swing arms, and the plurality of cooperative structures are in one-to-one correspondence with the insertion grooves; a center hole is defined by the arc-shaped abutting parts at the second ends of the connecting rods of the plurality of cooperative structures of the elastic pieces, the connecting rods and the swing arms, and the pin penetrates through the center hole.

Furthermore, the center hole is of a flared structure which gradually becomes wider from top to bottom.

Furthermore, an insertion end of the pin is of a conical guide structure.

Furthermore, the recessing openings are formed in opposite side walls of each insertion groove; the number of the swing arms is two, and the two swing arms are symmetrically arranged; the second ends of the two swing arms are pivoted to the corresponding connecting rod, and the inner container protrusions at the first ends of the two swing arms correspond to the recessing openings in the opposite side walls of the corresponding insertion groove.

Furthermore, the swing arms are integrally connected with the inner container protrusions.

By adoption of the above technical solution, the invention has the following beneficial effects:

When the filter element is installed, the filter element is placed on the outer cover which is then inserted into the insertion grooves of the bottom bracket through the insertion rods, and then the driving part of the limiting structure is controlled to drive the inner container protrusions to be inserted into the installation grooves of the insertion rods via the recessing openings of the insertion grooves to realize limiting, so that the outer cover is fixed and cannot be pulled out. When the filter element needs to be replaced, the driving part of the limiting structure is controlled to drive the inner container protrusions to disengage from the installation grooves of the insertion rods to retreat into the center cavity, so that the outer cover is released and can be disassembled, and the filter element can be replaced conveniently. The air purifier housing has the advantages of being easy and convenient to assemble and disassemble.

DETAILED DESCRIPTION OF THE INVENTION

Figure 1:
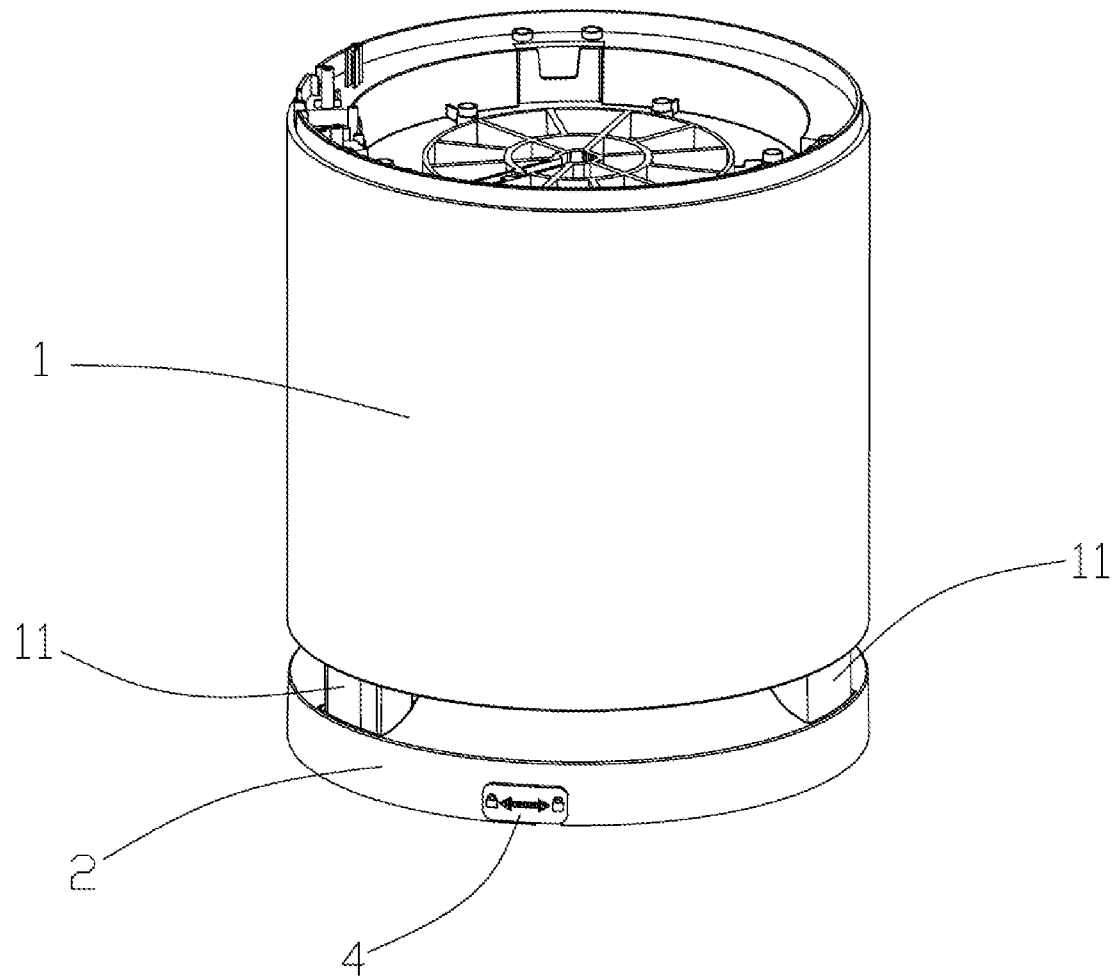
FIG. 1 is an assembled front view of Embodiment 1.

The accompanying drawings are provided for a further description of embodiments of the invention. These drawings are part of the contents disclosed by the invention and are mainly used for illustrating the embodiments and explaining the operating principle of the embodiments in cooperation with relevant description in the specification. By referring to these contents, those ordinarily skilled in this field can appreciate other possible implementations and advantages of the invention. The components in these drawings are not drawn in scale, and similar reference signs represent similar components.

The invention is further described below with reference to the accompanying drawings and specific implementations.

The air purifier housing of the invention is illustrated by being applied to an air purifier. Implementations and appropriate adjustments of the invention by those skilled in the art according to actual applications should not be regarded as limitations to the invention.

The invention provides an air purifier housing which comprises an outer cover and a bottom bracket. A center cavity which is open downwards is formed in the bottom bracket. Insertion grooves are formed in the bottom bracket. Recessing openings stretching to the center cavity are formed in side walls of the insertion grooves. Insertion rods are fixedly arranged on the outer cover. The outer cover is inserted into the insertion grooves of the bottom bracket through the insertion rods. Installation grooves corresponding to the recessing openings are formed in the insertion rods. A limiting structure is arranged in the center cavity of the bottom bracket and comprises a driving part and inner container protrusions, wherein the inner container protrusions correspond to the recessing openings, the driving part is connected with the inner container protrusions and drives the inner container protrusions to reach a first position where the inner container protrusions stretch out of the insertion grooves to be inserted into the installation grooves of the insertion rods or to reach a second position where the inner container protrusions retreat into the center cavity.

When a filter element is installed, the filter element is placed on the outer cover which is inserted into the insertion grooves of the bottom bracket through the insertion rods, and then the driving part of the limiting structure is controlled to drive the inner container protrusions to be inserted into the installation grooves of the insertion rods via the recessing openings of the insertion grooves to realize limiting (namely, the inner container protrusions are located at the first position), so that the outer cover is fixed and cannot be pulled out. When the filter element needs to be replaced, the driving part of the limiting structure is controlled to drive the inner container protrusions to disengage from the installation grooves of the insertion rods to retreat into the center cavity (namely, the inner container protrusions are located at the second position), so that the outer cover is released and can be disassembled, and the filter element can be replaced conveniently. The air purifier housing has the advantages of being easy and convenient to assemble and disassemble.

A more detailed description of the invention is given below in combination with the following embodiments.

Embodiment 1

As shown in FIGS. 1-4, the air purifier housing in this embodiment comprises an outer cover 1, a bottom bracket 2 and a rotary convex platform 3, wherein a circular center cavity 21 which is open downwards is formed in the bottom bracket 2, at least one installation part 211 extending inwards is formed on the inner wall of the center cavity 21, and the rotary convex platform 3 is adaptively and rotatably arranged in the center cavity 21 and is provided with recessing regions 31 allowing the installation parts 211 to be recessed therein and having a recessing area larger than the area of the installation parts 211; an L-shaped groove 2111 having a first end stretching to the top of the bottom bracket and a second end stretching into the center cavity 21 is formed in each installation part 211, and the L-shaped grooves 2111 serve as the insertion groove; the second ends of the L-shaped grooves 2111 are formed with the recessing openings and stretch into the center cavity 21; the recessing regions 31 of the rotary convex platform 3 extend towards the second ends of the L-shaped grooves 2111 to form rotary inner container protrusions 311, and the rotary inner container protrusions 311 serve as the inner container protrusions; the rotary inner container protrusions 311 extend towards the second ends of the L-shaped grooves 2111 from the recessing regions of the rotary convex platform 3; insertion rods 11 are fixedly arranged on the outer cover 1, wherein the number of the insertion rods 11 is consistent with that of the L-shaped grooves 2111, the insertion rods 11 are adaptively inserted into the first ends of the L-shaped grooves 2111, and installation grooves 111 corresponding to the second ends of the L-shaped grooves 2111 are formed in the insertion rods 11; when the rotary convex platform 3 is driven to rotate, the rotary inner container protrusions 311 enter the installation grooves 111 via the second ends of the L-shaped grooves 2111, and at this moment, inner walls 312 of the recessing regions are attached to inner walls of the installation parts to realize limiting in the rotation direction; stop blocks 212 are formed on the inner wall of the center cavity 21 of the bottom bracket 2, and engaging points 32 are formed on the periphery of the rotary convex platform 3; either the stop blocks 212 or the engaging points 32 are convex arc pieces (either the stop blocks 212 or the engaging points 32 are convex arc pieces which can stretch across the other components under the effect of an external force); and when the recessing regions 31 are attached to the installation parts 211 to realize limiting in the rotation direction, the stop blocks 212 prevent the engaging points 32 from moving in a direction opposite to the rotation direction so as to ensure limiting. When a filter element needs to be replaced, the rotary convex platform is rotated in a reverse direction, then the engaging points retreat to be separated from the stop blocks 212, the rotary inner container protrusions disengage from the installation grooves and the L-shaped grooves at the same time, at this moment, the outer cover can be detached from the bottom bracket with a small upward force, then the filter element to be replaced is taken out of the center cavity, and a new filter element is placed on the upper surface of the bottom bracket; afterwards, the outer cover is assembled (namely, the insertion rods are inserted into the L-shaped grooves), a rotary inner container is rotated in a forward direction, then the rotary inner container protrusions enter the installation grooves via the L-shaped grooves, the engaging points stretch to be attached to the stop blocks, and the engaging points cannot automatically retreat to be separated from the stop blocks in the absence of an external force, so that full locking is realized. The air purifier housing has the advantages of being easy and convenient to assemble and disassemble.

In this embodiment, the rotary convex platform 3 serves as the driving part of the limiting structure and can be rotated to drive the rotary inner container protrusions 311 (namely the inner container protrusions) to reach a first position where the rotary inner container protrusions 311 stretch out of the insertion grooves (namely the L-shaped grooves 2111) to be inserted into the installation grooves 111 of the insertion rods 11 to realize limiting or to reach a second position where the rotary inner container protrusions 311 disengage from the installation grooves 111 of the insertion rods 11 to retreat into the center cavity cancel limiting.

In this embodiment, the number of the insertion rods 11, the L-shaped grooves 2111, the installation parts 211 and the recessing regions 31 is greater than one (in this embodiment, the number of the insertion rods 11, the L-shaped grooves 2111, the installation parts 211 and the recessing regions 31 is three, so that the stability is good, and the cost is low; and the invention has no limitation in this aspect, the number of the insertion rods 11, the L-shaped grooves 2111, the installation parts 211 and the recessing regions 31 can also be two or four in other embodiments, and details will not be given anymore herein), and the installation parts 211 are arranged at intervals around the center of the center cavity 21.

Figure 2:
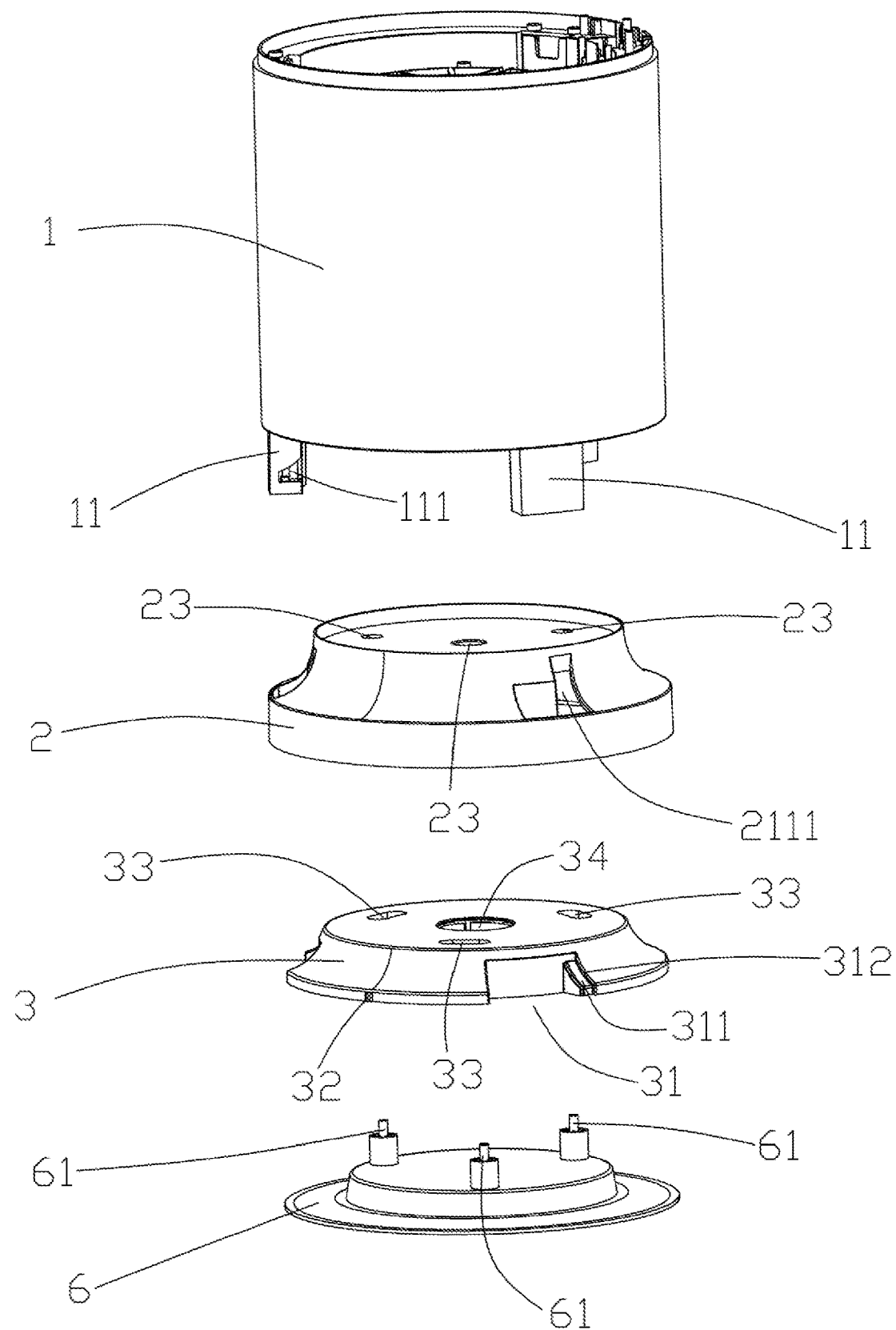
FIG. 2 is an exploded view of Embodiment 1.
Figure 3:
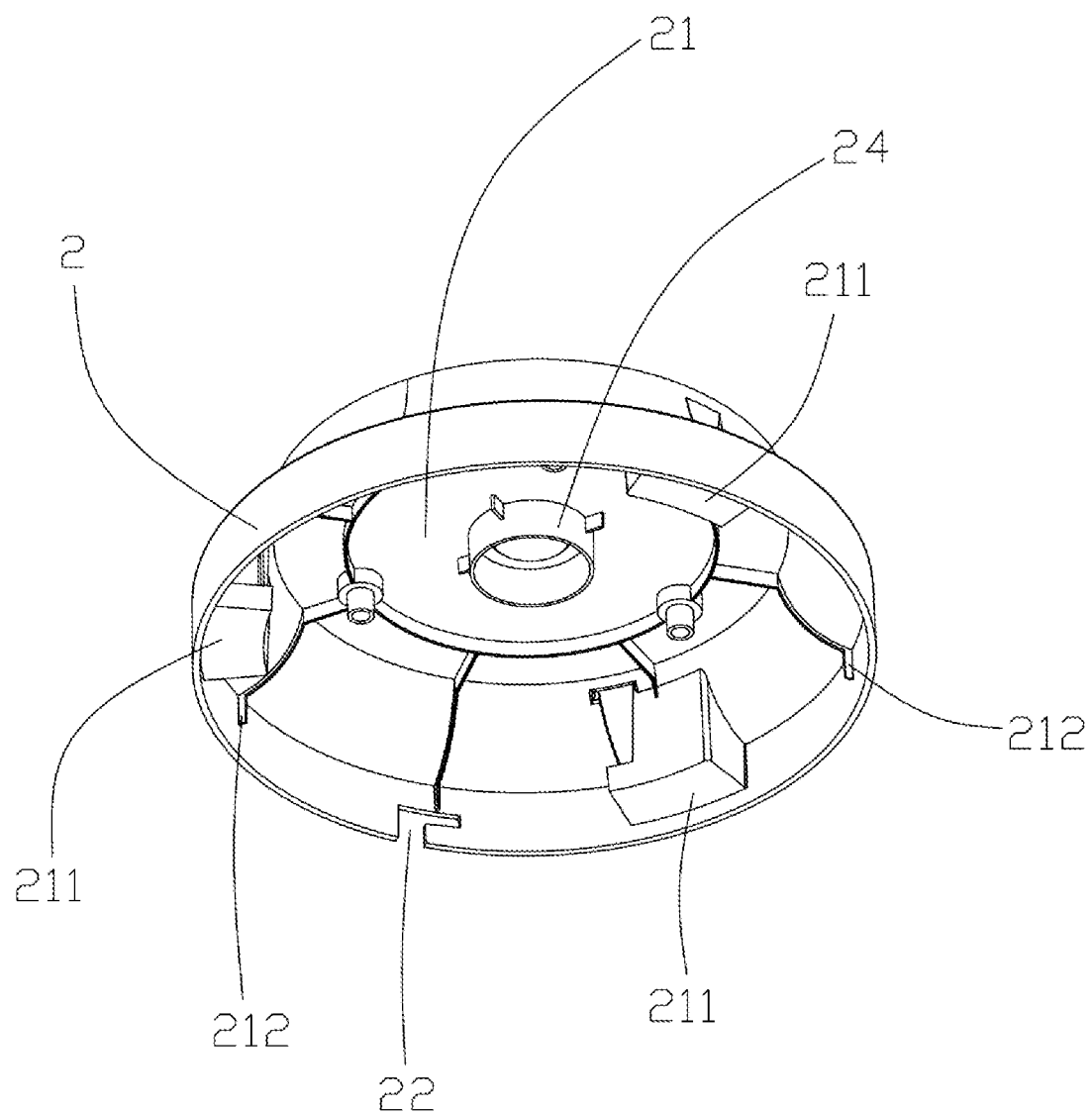
FIG. 3 is a perspective view of a bottom bracket in Embodiment 1.
Figure 4:
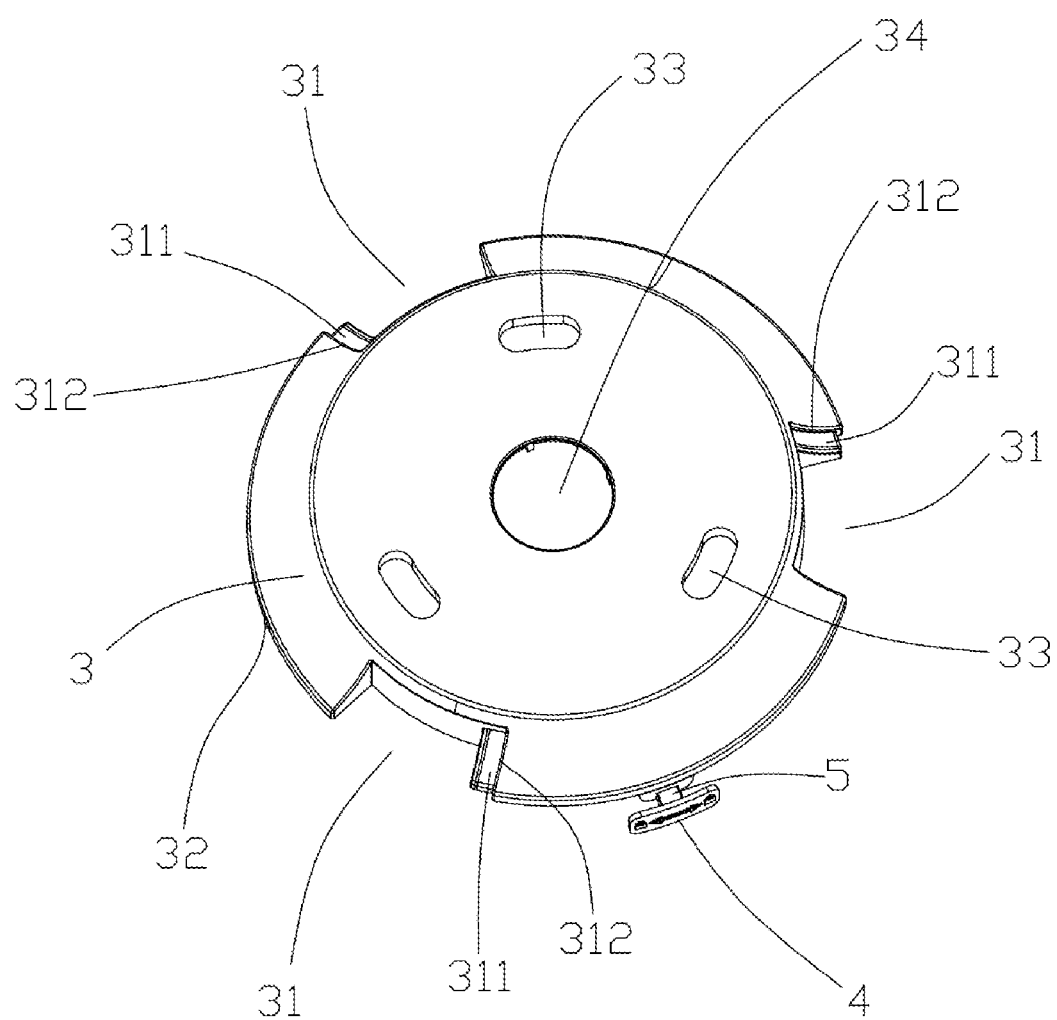
FIG. 4 is a perspective view of a rotary convex platform in Embodiment 1.
Figure 5:
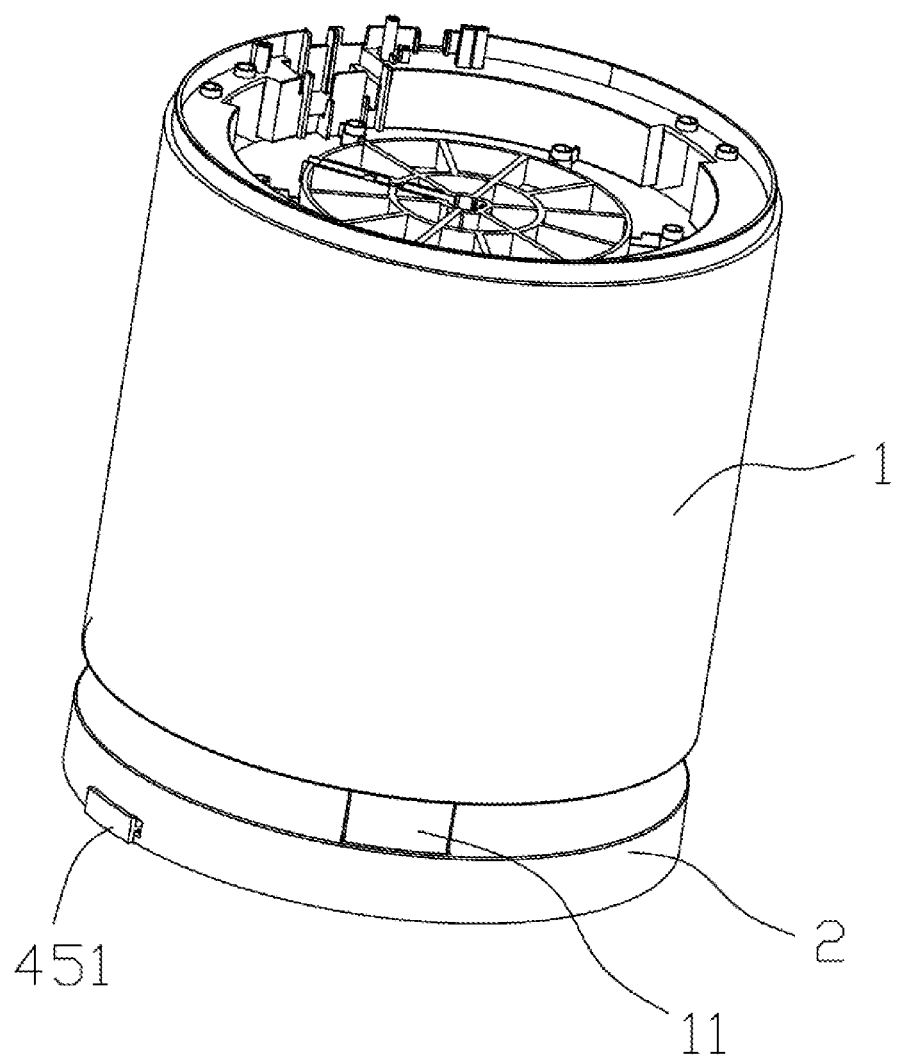
FIG. 5 is an assembled front view of an air purifier housing in Embodiment 2.
Figure 6:
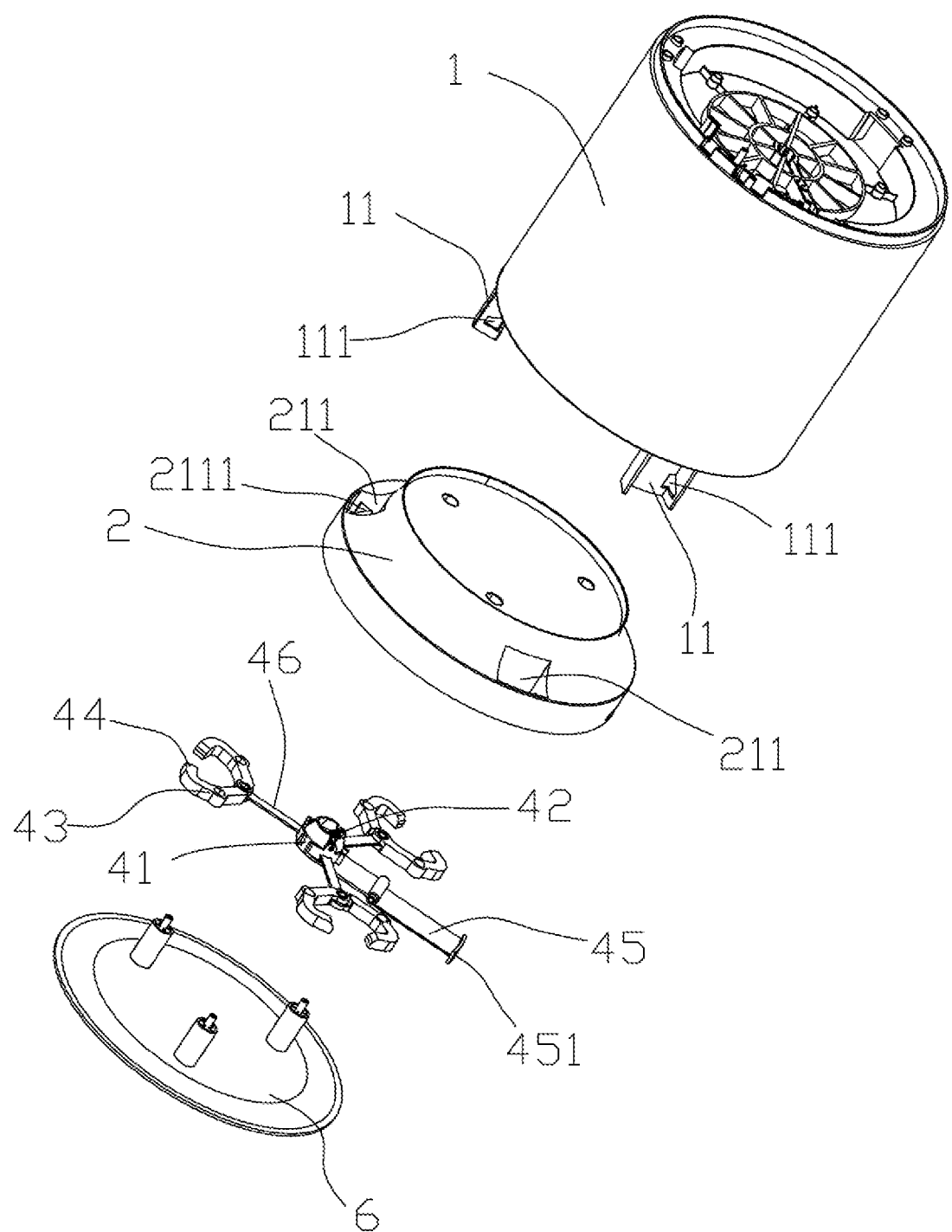
FIG. 6 is an exploded view of the air purifier housing in Embodiment 2.
Figure 7:
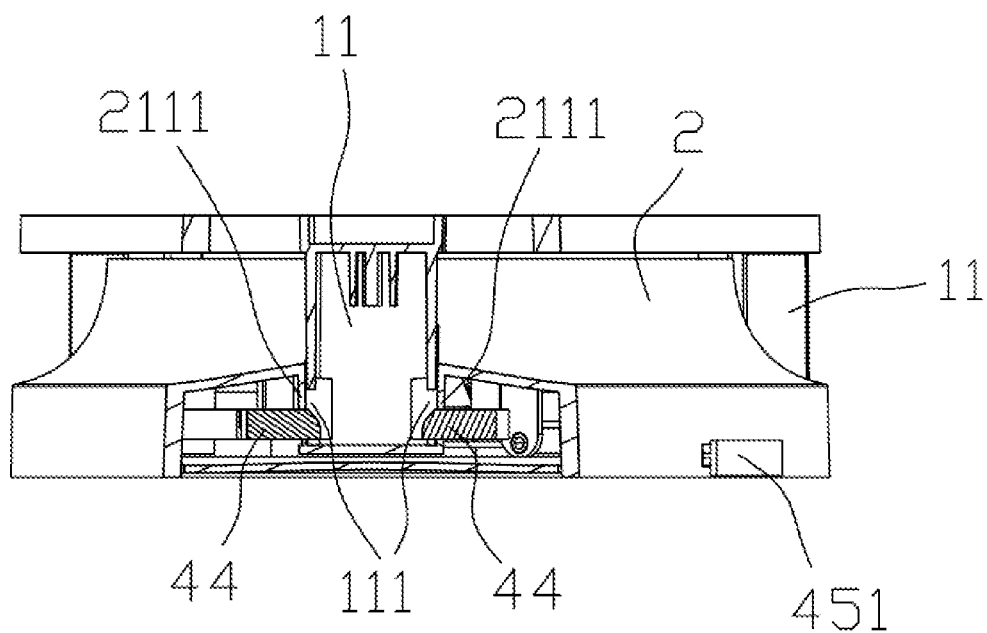
FIG. 7 is a sectional view of the air purifier housing in Embodiment 2 when inner container protrusions are located at a first position.
Figure 8:
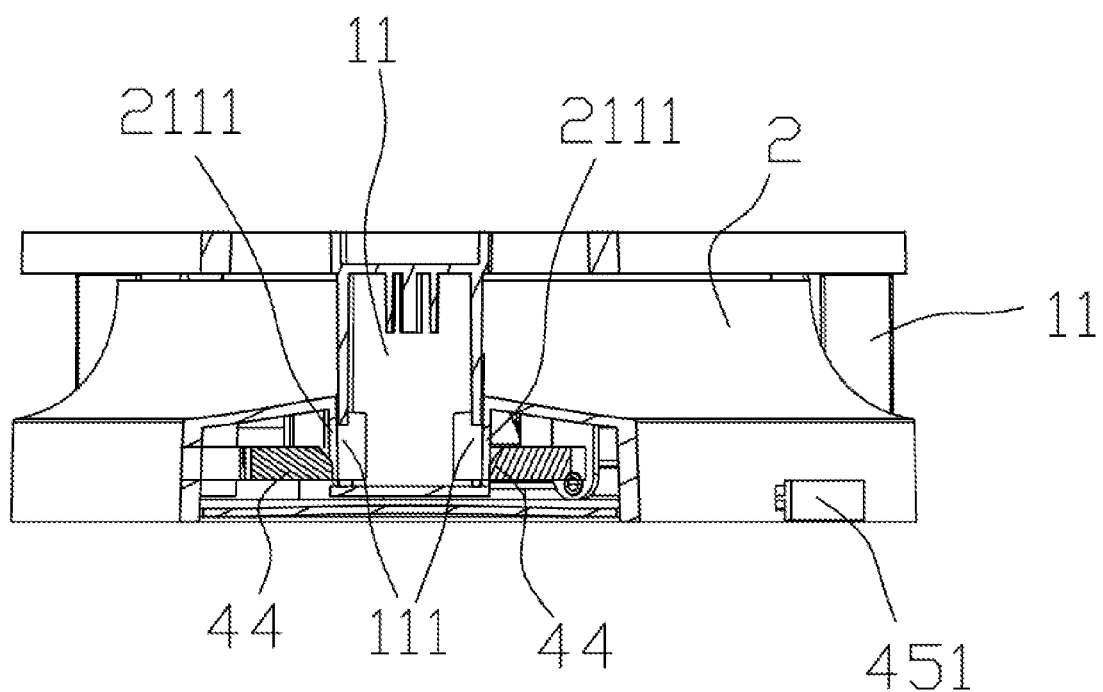
FIG. 8 is a sectional view of the air purifier housing in Embodiment 2 when the inner container protrusions are located at a second position.
Figure 9:
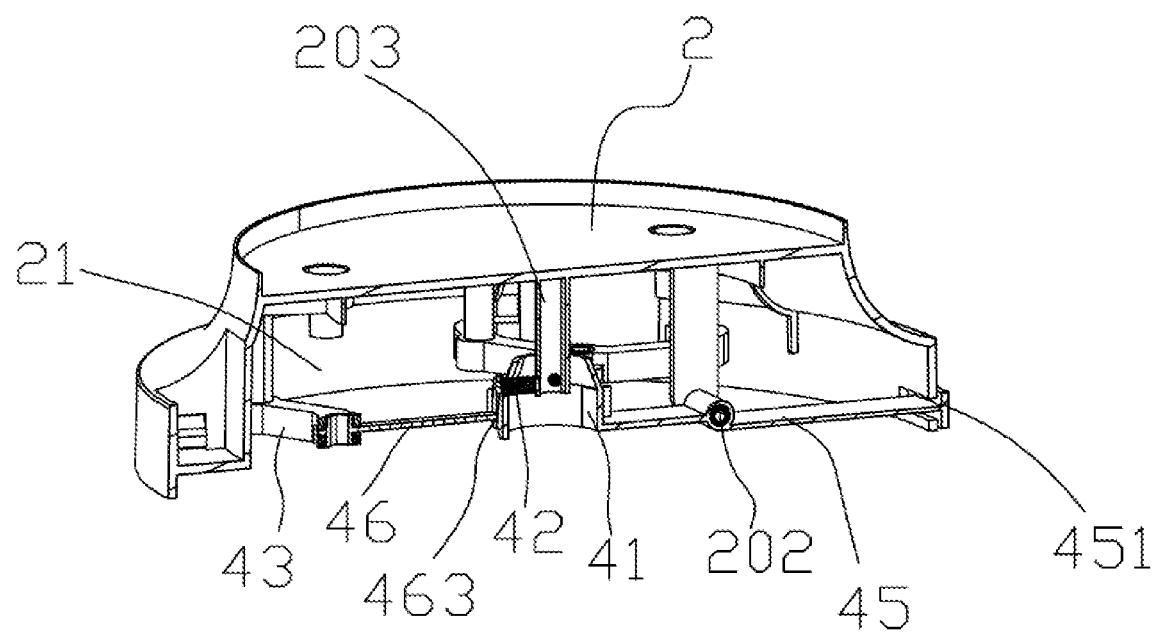
FIG. 9 is a first internal sectional view of the bottom bracket in Embodiment 2.
Figure 10:
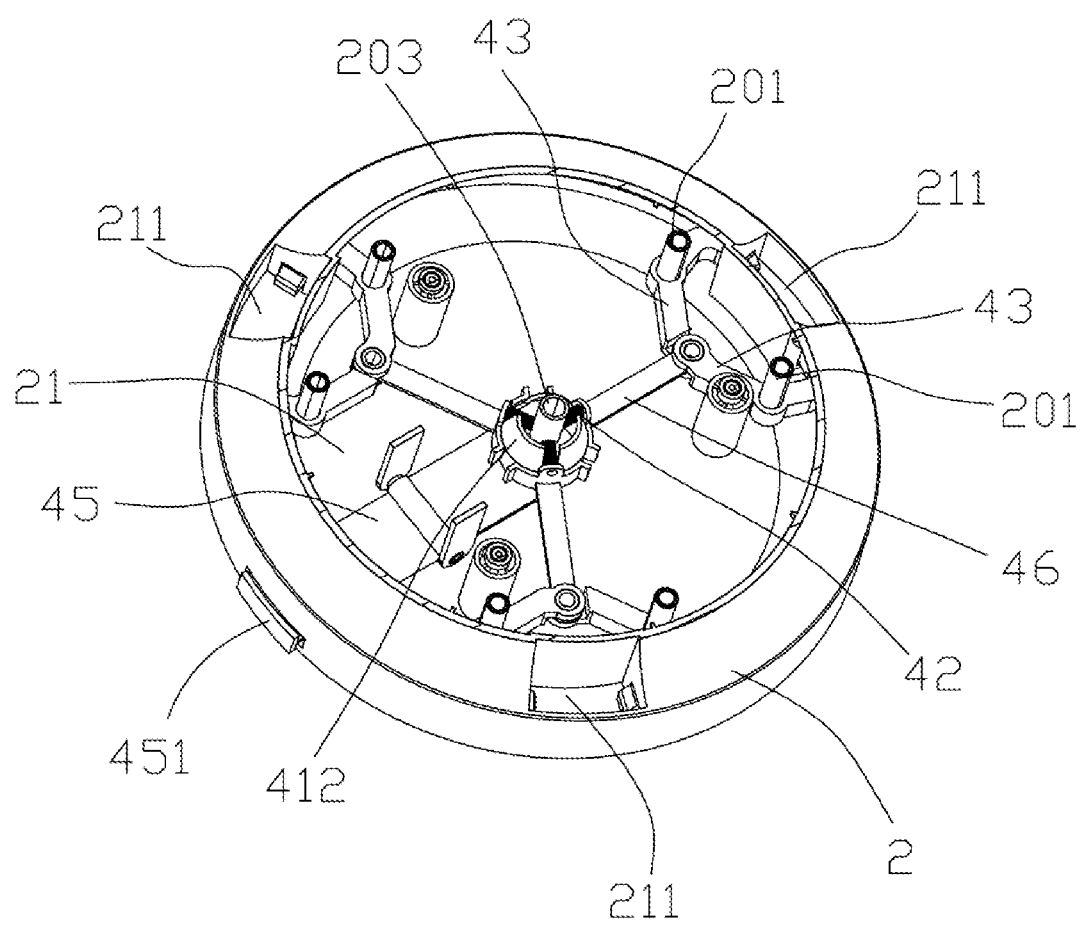
FIG. 10 is a second internal sectional view of the bottom bracket in Embodiment 2.
Figure 11:
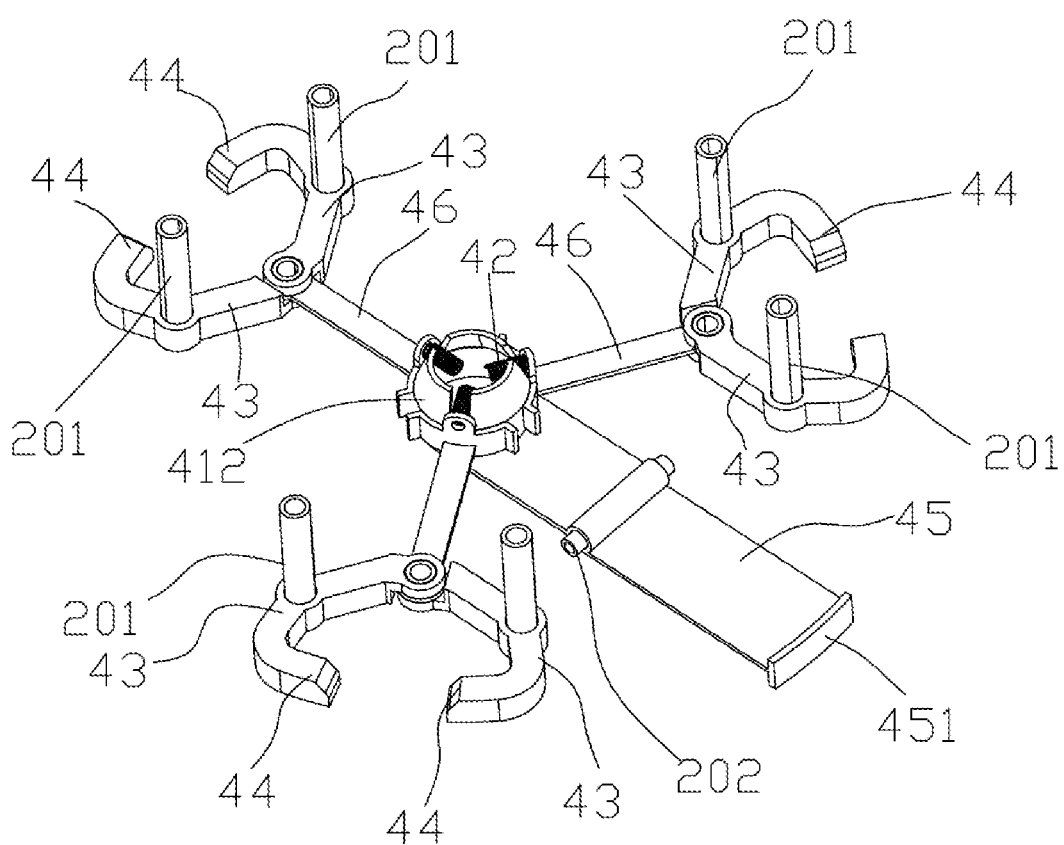
FIG. 11 is an assembled view of a limiting structure in Embodiment 2.
Figure 12:
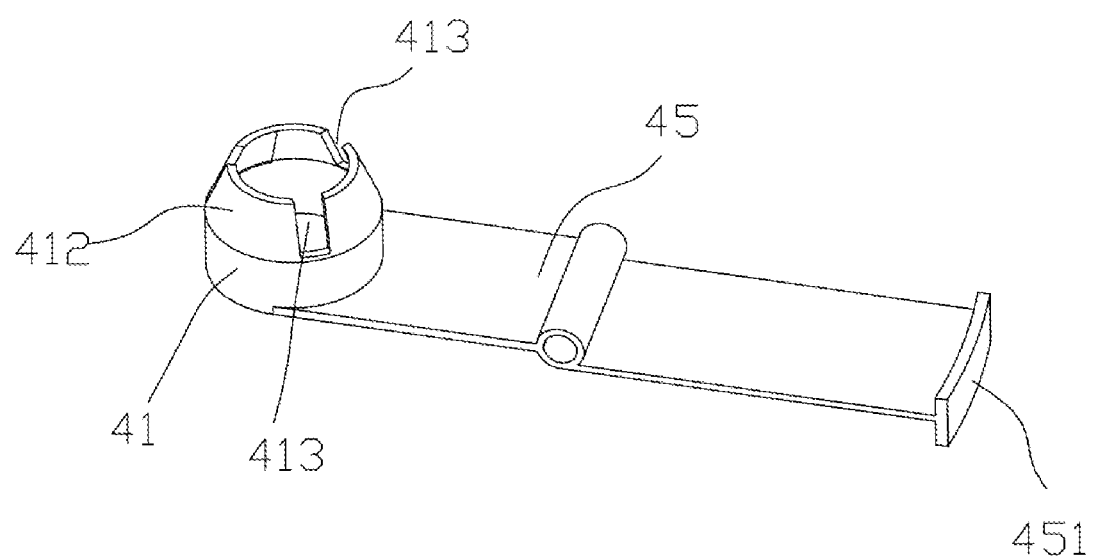
FIG. 12 is a connection diagram of a bolt and a toggle rod in Embodiment 2.
Figure 13:
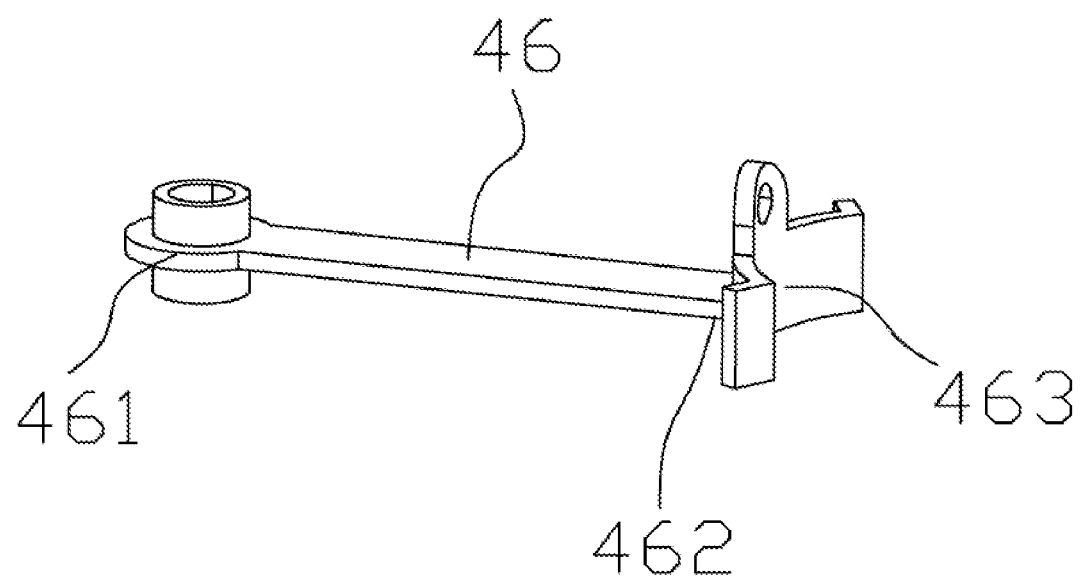
FIG. 13 is a connection diagram of a connecting rod in Embodiment 2.
Figure 14:
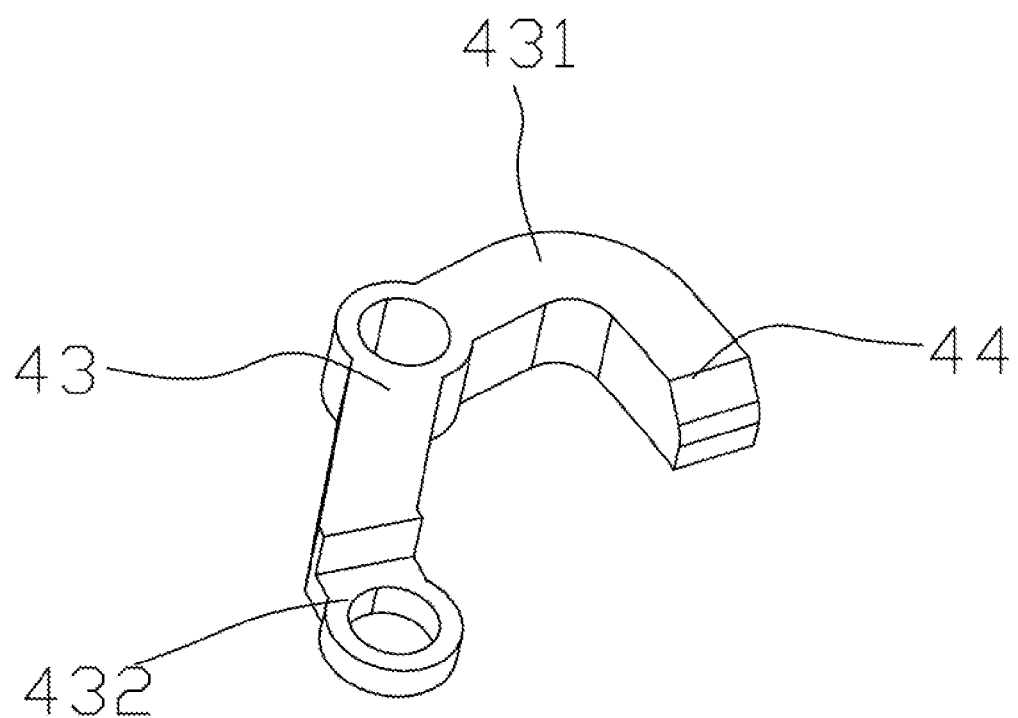
FIG. 14 is a connection diagram of a swing arm and an inner container protrusion in Embodiment 2.

As shown in FIGS. 2-4, either the stop blocks 212 or the engaging points 32 are semicircular, and the other ones are in a long strip shape (in this embodiment, the engaging points 32 are semicircular, and the stop blocks 212 are in a long strip shape; or, the stop blocks 212 are semicircular and the engaging points 32 are in a long strip shape in other embodiments, and the invention has no limitation in this aspect); and the number of the stop blocks 212 is consistent with that of the installation parts 211, and each stop block 212 is arranged between two installation parts 211.

As shown in FIG. 4, the air purifier housing further comprises a drive knob 4 which is fixedly arranged on the periphery of the rotary convex platform 3 and stretches out of the bottom bracket 2, and a first recessing hole 22 allowing the drive knob to be recessed therein is formed in the bottom bracket 2. When a clockwise or anticlockwise external force is applied to the drive knob 4, the rotary convex platform 3 clockwise or anticlockwise rotates relative to the bottom bracket 2.

As shown in FIG. 3, the first recessing hole 22 is in an inverted-L shape, and the drive knob 4 is fixedly connected to the periphery of the rotary convex platform 3 through a connector 5 capable of adaptively moving in the first recessing hole 22.

As shown in FIG. 2, the air purifier housing further comprises a base 6, wherein the base 6 is fixedly arranged in the center cavity 21 of the bottom bracket 2, and the bottom of the base 6 is adaptively flush with and attached to an opening of the center cavity 21 of the bottom bracket 2. Preferably, locking pieces 61 extending upwards are arranged on the base 6, second recessing holes 33 allowing the locking pieces 61 to be recessed therein are formed in the rotary convex platform 3, third recessing holes 23 allowing the locking pieces 61 to be recessed therein are formed in the bottom bracket 2, threaded parts are arranged at upper ends of the locking pieces 61, and after sequentially penetrating through the second recessing holes 33 and the third recessing holes 23, the threaded parts at the upper ends of the locking pieces 61 are locked with nuts, so that the bottom bracket 2 and the base 6 are fixed together.

As shown in FIG. 2, the number of the locking pieces 61 is at least two (the number of the locking pieces 61 is three in this embodiment; the invention has no limitation in this aspect, and the number of the locking pieces 61 can be two or four in other embodiments, and details will not be given anymore herein), and the locking pieces 61 are arranged at intervals around the base 6.

As shown in FIG. 2 and FIG. 4, the second recessing holes 33 are long strip-shaped holes, so that the position of the rotary convex platform 3 can be adjusted in the installation process, and certain assembly errors are permissible.

As shown in FIG. 3 and FIG. 4, a circular blind hole which is open downwards is formed in the center of the bottom bracket 2, and the blind hole serves as the center cavity; and a positioning block 24 extending downwards is formed at the center of the inner wall of the upper end of the center cavity, and a positioning hole 34 allowing the positioning block 24 to be adaptively inserted therein is formed in the center of the rotary convex platform 3. The configuration of the positioning block 24 and the positioning hole 34 facilitates alignment of the locking pieces 61 to the second recessing holes 33 and the third recessing holes 23 in the assembly process.

When the filter element needs to be replaced, the rotary convex platform is rotated in the reverse direction, so that the engaging points retreat to be separated from the stop blocks, the rotary inner container protrusions disengage from the installation grooves and the L-shaped grooves at the same time, at this moment, the outer cover can be detached from the bottom bracket with a small upward force, then the filter element to be replaced is taken out of the center cavity, and a new filter element is placed on the upper surface of the bottom bracket; afterwards, the outer cover is assembled (namely, the insertion rods are inserted into the L-shaped grooves), the rotary inner container is rotated in the forward direction, the rotary inner container protrusions enter the installation grooves via the L-shaped grooves, the engaging points stretch in the forward direction to be attached to the stop blocks, and the engaging points cannot retreat to be separated from the stop blocks in the absence of an external force, so that full locking is realized. The air purifier housing has the advantages of being easy and convenient to assemble and disassemble.

Embodiment 2

As shown in FIGS. 5-14, the air purifier housing in this embodiment comprises an outer cover 1 and a bottom bracket 2, wherein a center cavity 21 which is open downwards is formed in the bottom bracket 2, insertion grooves 211 are formed in the bottom bracket 2, recessing openings 2111 stretching into the center cavity 21 are formed in side walls of the insertion grooves 211, insertion rods 11 are fixedly arranged on the outer cover 1, the outer cover 1 is inserted into the insertion grooves 211 of the bottom bracket 2 through the insertion rods 11, and installation grooves 111 corresponding to the recessing openings 2111 are formed in the insertion rods 11.

A limiting structure is arranged in the center cavity 21 of the bottom bracket 2 and comprises swing arms 43, a driving part and inner container protrusions 44, wherein the swing arms are pivoted to first stationary shafts 201 in the center cavity 21, the inner container protrusions 44 are connected with the swing arms 43 and correspond to the recessing openings 2111, the driving part is connected with the swing arms 43 and drives the swing arms 43 to swing, the swing arms 43 swing to drive the inner container protrusions 44 to reach a first position where the inner container protrusions 44 stretch out of the insertion grooves 211 to be inserted into the installation grooves 111 of the insertion rods 11 or to reach a second position where the inner container protrusions 44 retreat into the center cavity 21.

The filter element is placed on the outer cover 1 which is then inserted into the insertion grooves 211 of the bottom bracket 2 through the insertion rods 11, and then the driving part controls the swing arms 43 to swing to drive the inner container protrusions 44 to be inserted into the installation grooves 111 of the insertion rods 11 via the recessing openings 2111 of the insertion grooves 211 to realize limiting or to drive the inner container protrusions 44 to disengage from the installation grooves 111 of the insertion rods 11 to retreat into the center cavity 21 to cancel limiting, so that the outer cover 1 is assembled or disassembled, and then the filter element can be replaced conveniently. The air purifier housing has the advantages of being easy and convenient to assemble and disassemble.

Furthermore, in this embodiment, the driving part comprises connecting rods 46, elastic pieces 42 and a pin 41, wherein second ends 432 of the swing arms 43 are pivoted to first ends 461 of the connecting rods 46, and the elastic pieces 42 always apply a force towards second ends 462 of the connecting rods 46 to the connecting rods 46 so as to drive the connecting rods 46 to move towards the second ends 462; the pin 41 is movably inserted to abut against the second ends 462 of the connecting rods 46 and drives the connecting rods 46 to overcome the force from the elastic pieces 42 to move towards the first ends 461; when moving back and forth towards the first ends 461 and the second ends 462, the connecting rods 46 drive the swing arms 43 to swing back and forth, and the swing arms 43 drive the inner container protrusions 44 to reach a first position (shown in FIG. 7) where the inner container protrusions 44 stretch out of the insertion grooves 211 to be inserted into the installation grooves 111 of the insertion rods 11 to realize limiting or to reach a second position (shown in FIG. 8) where the inner container protrusions 44 disengage from the installation grooves 111 of the insertion rods 11 to retreat into the center cavity 21 to cancel limiting.

When the filter element is installed, the filter element is placed on the outer cover 1 which is then inserted into the insertion grooves 211 of the bottom bracket through the insertion rods 11, and then the pin 41 is controlled to move to drive the inner container protrusions 44 to be inserted into the installation grooves 111 of the insertion rods 11 via the recessing openings 2111 of the insertion grooves 211 to realize limiting, so that the outer cover is fixed and is prevented from being pulled out; and when the filter element needs to be replaced, the pin 41 is controlled to move again to drive the inner container protrusions 44 to disengage from the installation grooves 111 of the insertion rods 11 to retreat into the center cavity 21 to cancel limiting, and then the outer cover 1 can be detached.

In this embodiment, the driving part comprises the connecting rods 46, the elastic pieces 42 and the pin 41, the elastic pieces 42 and the pin 41 are used to drive the swing arms 43 to swing, and the structure is simple. Clearly, in other embodiments, other drive components capable of driving the swing arms 43 to swing can also be adopted.

Furthermore, in this embodiment, the limiting structure is configured in such a manner: when the connecting rods 46 move towards the second ends 462, the swing arms 43 are driven to swing to drive the inner container protrusions 44 to reach a first position where the inner container protrusions 44 stretch out of the insertion grooves 211 to be inserted into the installation grooves 111 of the insertion rods 11 to realize limiting; and when the connecting rods 46 move towards the first ends 461, the swing arms 43 are driven to swing to drive the inner container protrusions 44 to reach a second position where the inner container protrusions 44 disengage from the installation grooves 111 of the insertion rods 11 to retreat into the center cavity 21 to cancel limiting. Namely, the inner container protrusions 44 are driven by the elastic pieces 42 to reach the second position and are driven by the pin 41 to reach the first position. When the air purifier housing needs to be disassembled, the pin 41 is inserted to abut against the second ends of the connecting rods 46 so as to enable the connecting rods 46 to move towards the first ends 461, then the inner container protrusions 44 are driven to disengage from the installation grooves 111 of the insertion rods 11 to retreat into the center cavity 21, and the insertion rods 11 are not restrained by the inner container protrusions 44 anymore and can be pulled out; after the filter element is replaced, the outer cover 1 is inserted into the insertion grooves 211 again through the insertion rods 11, at this moment, the pin 41 is moved to not abut against the second ends of the connecting rods 46 anymore, and the connecting rods 46 move towards the second ends 462 under the effect of the elastic pieces 42, so that the inner container protrusions 44 return to the first position again to limit and fix the outer cover 1.

Clearly, in other embodiments, the limiting structure can also be configured in such a manner: when the connecting rods 46 move towards the second ends 462, the swing arms 43 are driven to swing to drive the inner container protrusions 44 to reach the second position where the inner container protrusions 44 disengage from the installation grooves 111 of the insertion rods 11 to retreat into the center cavity 21 to cancel limiting; and when the connecting rods 46 move towards the first ends 461, the swing arms 43 are driven to swing to drive the inner container protrusions 44 to reach the first position where the inner container protrusions 44 stretch out of the insertion grooves 211 to be inserted into the installation grooves 111 of the insertion rods 11 to realize limiting. The limiting structure can be configured by those skilled in the art according to actual conditions. For instance, the extension direction of the inner container protrusions can be changed, namely the inner container protrusions extend in the reverse direction.

Particularly, in this embodiment, the first stationary shafts 201 extend into the center cavity 21 from the bottom bracket 2. In other embodiments, the first stationary shafts can be configured in other manners.

Particularly, in this embodiment, the outer cover 1 comprises a frame provided with the insertion rods 11, and a cover body provided with an installation cavity, wherein the frame is detachably and fixedly connected with the cover body, and the filter element is installed in the installation cavity of the cover body. In other embodiments, the outer cover 1 can be of other structures.

Furthermore, in this embodiment, the driving part further comprises a toggle rod 45, wherein the middle of the toggle rod 45 is pivoted to a second stationary shaft 202 in the center cavity 21, a first end of the toggle rod 45 is connected with the pin 41, and a second end of the toggle rod 45 extends out of the bottom bracket 2 to form a toggle button 451, so that a lever structure is formed. When the toggle button 451 is pulled downwards, the pin 41 moves upwards to be inserted to abut against the second ends 462 of the connecting rods 46, and then the connecting rods 46 are driven to move towards the first ends 461, so that the inner container protrusions 44 are driven to reach the second position where the inner container protrusions 44 disengage from the installation grooves 111 of the insertion rods 11 to retreat into the center cavity 21 to cancel limiting. When the toggle button 451 is pulled upwards, the pin 41 moves downwards, the second ends 462 of the connecting rods 46 are released by the pin 41 and move towards the second ends 462 under the effect of the elastic pieces 42, and then the inner container protrusions 44 are driven to reach the first position where the inner container protrusions 44 stretch out of the insertion grooves 211 to be inserted into the installation grooves 222 of the insertion rods 22 to realize limiting. The toggle button 451 used to control the pin 41 is simple in structure and easier and more convenient to operate.

Furthermore, in this embodiment, the elastic pieces 42 are tension springs, and a stationary connecting column 203 is arranged in the center cavity 21. Particularly, the stationary connecting column 203 extends into the center cavity 21 from the bottom bracket 2, the pin 41 is of a hollow structure and is disposed around the stationary connecting column 203, first ends of the tension springs 42 are fixedly connected to the stationary connecting column 203, second ends of the tension springs 42 are connected to the second ends 462 of the connecting rods 46, recessing notches 413 allowing the tension springs 42 to be recessed therein are formed in the pin 41; and a pulling force from the tension springs 42 drive the connecting rods 46 to move towards the second ends 462 of the connecting rods 46; and when inserted, the pin 41 abuts against the second ends 462 of the connecting rods 46 so as to drive the connecting rods 46 to move towards the first ends 461. Clearly, in other embodiments, the elastic pieces can also be other structures such as compression springs or V-shaped elastic pieces which can apply a force towards the second ends to the connecting rods.

Furthermore, in this embodiment, arc-shaped abutting parts 463 matched with the outer wall of the pin 42 are formed at the second ends 462 of the connecting rods 46, the connecting rods 46 adaptively abut against the pin 41 through the arc-shaped abutting parts 463, and the pin can be half wrapped by the arc-shaped abutting parts 463, so that the connecting rods 46 and the pin 41 are matched more stably and are unlikely to be separated. Clearly, in other embodiments, the connecting rods 46 and the pin 41 can be replaced with other structures capable of achieving positioning and guiding.

Furthermore, in this embodiment, the number of the insertion grooves 211 is more than one, the limiting structure is provided with a plurality of cooperative structures of elastic pieces 42, connecting rods 46 and swing arms 43, and the plurality of cooperative structures of elastic pieces 43, connecting rods 46 and swing arms 63 are in one-to-one correspondence with the insertion grooves 211; and in the plurality of cooperative structures of elastic pieces 43, connecting rods 46 and swing arms 63, the arc-shaped abutting parts 463 of the second ends 462 of the connecting rods 46 define a center hole, and the pin 41 penetrates through the center hole. When the outer cover 1 needs to be disassembled, the pin 41 is inserted into the center hole to expand the center hole, so that the second ends 462 of the connecting rods 46 abut against the pin 41, and then the connecting rods 46 are driven by the pin 41 to move towards the first ends 461. In this way, multiple inner container protrusions 44 can be driven by one pin 41 to move at the same time. Clearly, in other embodiments, the plurality of cooperative structures of elastic pieces, connecting rods and swing arms of the limiting structure can also be respectively driven by a plurality of pins.

Particularly, the number of the insertion grooves 211 is three, and correspondingly, the limiting structure is provided with three cooperative structures of elastic pieces 42, connecting rods 46 and swing arms 43. In other embodiments, the number of the insertion grooves 211 and the number of cooperative structures of elastic pieces 42, connecting rods 46 and swing arms 43 of the limiting structure can be one, two, or more according to actual conditions.

Furthermore, in this embodiment, an insertion end 412 of the pin 41 is of a conical guide structure having a guide function. When the pin 41 starts to be inserted, the insertion end 412 of the conical guide structure makes contact with the second ends 462 of the connecting rods 46. When the pin 41 continues to be entirely inserted, the insertion end 412 gradually pushes away the connecting rods 46, that is to say, the connecting rods 46 are gradually driven to move towards the first ends 461 of the connecting rods 46. By adoption of the conical guide structure of the insertion end 412 of the pin 41, the structure is simple, and operation is smoother. Clearly, in other embodiments, oblique guide faces (not shown) can be formed at the second ends 462 of the connecting rods 46 to be matched with the pin, that is to way, the arc-shaped abutting parts at the second ends are set as oblique guide faces. The center hole defined by the arc-shaped abutting parts 463 of the connecting rods 46 is of a flared structure (not shown) which gradually becomes wider from top to bottom, so as to be matched with the pin.

Furthermore, the air purifier housing in this embodiment further comprises a bottom cover 6 which is fixed in a bottom opening of the center cavity 21 of the bottom bracket 2 to cover the bottom bracket 2. Particularly, corresponding connecting columns extending outwards are formed in the bottom bracket 2 and the bottom cover 6, corresponding connecting holes are formed in the connecting columns, fasteners (such as bolts) penetrates through the connecting holes to fulfill fixation and connection, and thus, the bottom cover 6 is fixed on the bottom bracket 2 in a covering manner. Clearly, in other embodiments, the bottom cover 6 can also be fixed on the bottom bracket 2 through a conventional method such as bonding, clamping or screwing, so as to cover the bottom bracket 2.

Furthermore, in this embodiment, recessing openings 2111 are formed in opposite side walls of each insertion groove 211, and each cooperative structure includes two symmetrical swing arms 43. The second ends of the two swing arms 43 in each cooperative structure are both pivoted to the corresponding connecting rod 46, and the inner container protrusions 44 at the first ends of the two swing arms 43 correspond to the recessing openings 2111 in the opposite side walls of the corresponding insertion groove 211. Each insertion rod 11 is inlaid and limited by two inner container protrusions 44 on the left side and right side, so that the structure is more stable. Clearly, in other embodiments, each insertion rod 11 can also be inlaid and limited through one inner container protrusion 44.

Furthermore, in this embodiment, the swings 43 are integrally connected with the inner container protrusions 44 and can be integrally manufactured more easily and conveniently through injection molding. Clearly, in other embodiments, the swing arms 43 and the inner container protrusions 44 can also be independent components and are connected through an assembly method.

Embodiment 3

Figure 15:
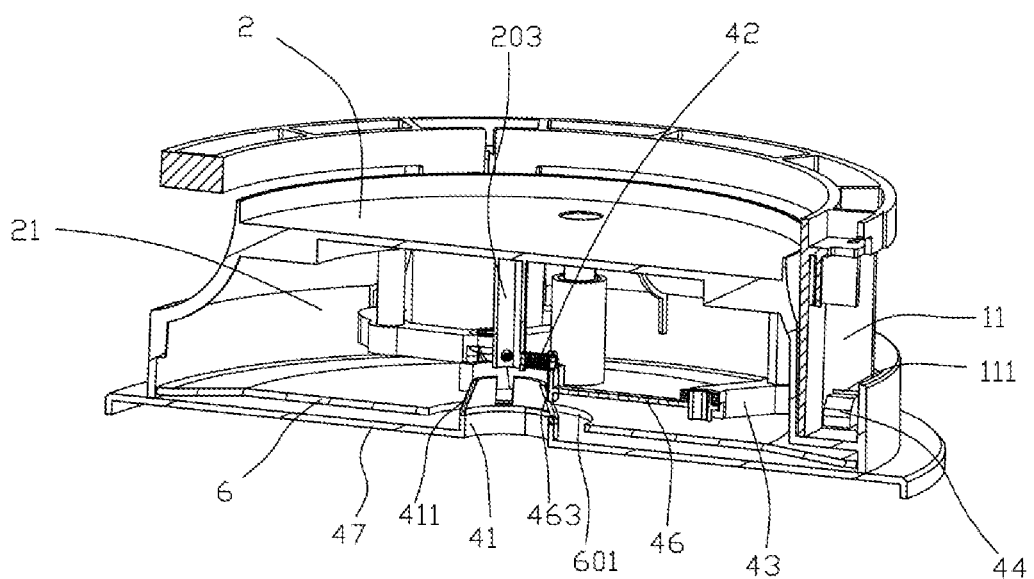
FIG. 15 is a structural sectional view of Embodiment 3.

The air purifier housing in this embodiment is basically identical with the air purifier housing in Embodiment 2 in structure and differs from the air purifier housing in Embodiment 2 in the following aspects: as shown in FIG. 15, in this embodiment, the pin 41 is pressed by an elastic base plate 47 to move instead of being controlled by the toggle button 451. Particularly, the driving part further comprises the elastic base plate 47, which covers a bottom opening of the center cavity 21 of the bottom bracket 2 and is fixedly connected with the pin 41, and the elastic base plate 47 can be elastically pressed towards the interior of the center cavity 21 to drive the pin 41 to be movably inserted. When the inner container protrusions 44 need to return to the second position, the elastic base plate 47 is pressed to elastically deform inwards (towards the interior of the center cavity 21) and then drives the pin 41 to be inserted, then the connecting rods 46 are driven to move towards the first ends 461 of the connecting rods 46, and the inner container protrusions 44 retreat into the center cavity 21. After the external force applied to the elastic base plate 47 is removed, the elastic base plate 47 restores to drive the pin 41 to be separated from the connecting rods 46, the connecting rods 46 move towards the second ends 462 under the effect of the elastic pieces 42, and then, the inner container protrusions 44 move to the first position. The elastic base plate 47 used for driving also has the characteristics of being simple in structure and easy and convenient to operate.

Furthermore, in this embodiment, the bottom cover 6 is reserved, and a through hole 601 allowing the pin 41 to penetrate through is formed in the center of the bottom cover 6. The bottom cover 6 is concaved towards the interior of the center cavity 21 to form a concave region allowing the elastic base plate 47 to be elastically pressed therein and having a limiting function to prevent the elastic base plate 47 from being excessively pressed. Clearly, in other embodiments, the bottom cover 6 can be omitted, and only the elastic base plate 47 is adopted.

The invention is specifically illustrated and explained with preferred embodiments. Those skilled in the art would appreciate that various variations of the invention can be made in forms and in details without deviating from the spirit and scope defined by the claims, and all these variations should also fall within the protection scope of the invention.

What is claimed is:

1. An air purifier housing, comprising an outer cover and a bottom bracket, wherein a center cavity which is open downwards is formed in the bottom bracket, insertion grooves are formed in the bottom bracket, recessing openings stretching into the center cavity are formed in side walls of the insertion grooves, insertion rods are fixedly arranged on the outer cover, the outer cover is inserted into the insertion grooves of the bottom bracket through the insertion rods, and installation grooves corresponding to the recessing openings are formed in the insertion rods; and a limiting structure is arranged in the center cavity of the bottom bracket and comprises a driving part and inner container protrusions, the inner container protrusions correspond to the recessing openings, and the driving part is connected with the inner container protrusions and drives the inner container protrusions to reach a first position where the inner container protrusions stretch out of the insertion grooves to be inserted into the installation grooves of the insertion rods or to reach a second position where the inner container protrusions retreat into the center cavity.

2. The air purifier housing according to claim 1, wherein the driving part of the limiting structure is a rotary convex platform, at least one installation part extending inwards is formed on an inner wall of the center cavity, and the rotary convex platform is adaptively and rotatably arranged in the center cavity and is provided with recessing regions allowing the installation parts to be recessed therein and having a recessing area larger than an area of the installation parts; an L-shaped groove having a first end stretching to a top of the bottom bracket and a second end stretching into the center cavity is formed in each said installation part, and the L-shaped grooves serve as the insertion grooves; the second ends of the L-shaped grooves are formed with the recessing openings and stretch into the center cavity, the inner container protrusions are rotary inner container protrusions, the recessing regions of the rotary convex platform extend towards the second ends of the L-shaped grooves to stretch out of the rotary inner container protrusions, and the insertion rods are 24 adaptively inserted into the first ends of the L-shaped grooves; when the rotary convex platform is driven to rotate, the rotary inner container protrusions enter the installation grooves via the second ends of the L-shaped grooves, inner walls of the recessing regions are gradually attached to inner walls of the installation parts to realize limiting in a rotation direction; stop blocks are formed on the inner wall of the center cavity of the bottom bracket, engaging points formed on a periphery of the rotary convex platform, and either the stop blocks or the engaging points are convex arc pieces; and when the recessing regions are attached to the installation parts to realize limiting in the rotation direction, the stop blocks prevent the engaging points from moving in a direction opposite to the rotation direction so as to ensure limiting.

3. The air purifier housing according to claim 2, wherein the number of the insertion rods, the L-shaped grooves, the installation parts and the recessing regions is greater than one, and the installation parts are arranged at intervals around a center of the center cavity.

4. The air purifier housing according to claim 3, wherein either the stop blocks or the engaging points are semicircular, and the other ones are in a long strip shape; and the number of the stop blocks is consistent with that of the installation parts, and each said stop block is arranged between two said installation parts.

5. The air purifier housing according to claim 2, wherein the air purifier housing further comprises a drive knob which is fixedly arranged on the periphery of the rotary convex platform and stretches out of the bottom bracket, and a first recessing hole allowing the drive knob to be recessed therein is formed in the bottom bracket.

6. The air purifier housing according to claim 5, wherein the first recessing hole is in an inverted-L shape, and the drive knob is fixedly connected to the periphery of the rotary convex platform through a connector capable of adaptively moving in the first recessing hole.

7. The air purifier housing according to claim 6, wherein the air purifier housing further comprises a base fixedly arranged in the center cavity of the bottom bracket, and a bottom of the base is adaptively flush with and attached to an opening of the center cavity of the bottom bracket.

8. The air purifier housing according to claim 7, wherein locking pieces extending upwards are arranged on the base, second recessing holes allowing the locking pieces to be recessed therein are formed in the rotary convex platform, and third recessing holes allowing the locking pieces to be recessed therein are formed in the bottom bracket.

9. The air purifier housing according to claim 8, wherein the number of the locking pieces is at least two, and the locking pieces are arranged at intervals around a center of the base.

10. The air purifier housing according to claim 1, wherein the limiting structure further comprises swing arms which are pivoted to first stationary shafts in the center cavity, the inner container protrusions are connected with the swing arms and correspond to the recessing openings, the driving part is connected with the swing arms and drives the swing arms to swing back and forth, and the swing arms drive the inner container protrusions to reach the first position where the inner container protrusions stretch out of the insertion grooves to be inserted into the installation grooves of the insertion rods or to reach the second position where the inner container protrusions retreat into the center cavity.

11. The air purifier housing according to claim 10, wherein the driving part comprises connecting rods, elastic pieces and a pin; middles of the swing arms are pivoted to the first stationary shafts in the center cavity, first ends of the swing arms are connected with the inner container protrusions, second ends of the swing arms are pivoted to first ends of the connecting rods, and the elastic pieces always apply a force towards second ends of the connecting rods to the connecting rods, so as to drive the connecting rods to move towards the second ends; the pin is movably inserted to abut against the second ends of the connecting rods and drives the connecting rods to overcome the force from the elastic pieces to move towards the first ends; and when the connecting rods move back and forth towards the first ends and the second ends, the swing arms are driven to swing back and forth, and then the inner container protrusions are driven to reach the first position or the second position.

12. The air purifier housing according to claim 11, wherein the driving part further comprises a toggle rod, a middle of the toggle rod is pivoted to a second stationary shaft in the center cavity, a first end of the toggle rod is connected with the pin, and a second end of the toggle rod extends out of the bottom bracket to form a toggle button.

13. The air purifier housing according to claim 11, wherein the driving part further comprises an elastic base plate, the elastic base plate covers a bottom opening of the center cavity of the bottom bracket and is fixedly connected with the pin, and the elastic base plate can be elastically pressed towards an interior of the center cavity to drive the pin to be movably inserted.

14. The air purifier housing according to claim 13, wherein the air purifier housing further comprises a bottom cover, and the bottom cover is fixedly arranged in the bottom opening of the center cavity of the bottom bracket in a covering manner; and a through hole allowing the pin to be recessed therein is formed in the center of the bottom cover, and the bottom cover is concaved towards the interior of the center cavity to form a concave region allowing the elastic base plate to be elastically pressed therein.

15. The air purifier housing according to claim 11, wherein the elastic pieces are tension springs, a stationary connecting column is arranged in the center cavity, the pin is of a hollow structure and is disposed around the stationary connecting column, first ends of the tension springs are fixedly connected to the stationary connecting column, second ends of the tension springs are fixedly connected to the second ends of the connecting rods, and recessing notches allowing the tension springs to be recessed therein are formed in the pin.

16. The air purifier housing according to claim 11, wherein arc-shaped abutting parts matched with an outer wall of the pin are formed at the second ends of the connecting rods.

17. The air purifier housing according to claim 16, wherein the number of the insertion grooves is more than one; the limiting structure is provided with a plurality of cooperative structures of the elastic pieces, the connecting rods and the swing arms, and the plurality of cooperative structures are in one-to-one correspondence with the insertion grooves; a center hole is defined by the arc-shaped abutting parts at the second ends of the connecting rods of the plurality of cooperative structures of the elastic pieces, the connecting rods and the swing arms, and the pin penetrates through the center hole.

18. The air purifier housing according to claim 17, wherein the center hole is of a flared structure which gradually becomes wider from top to bottom.

19. The air purifier housing according to claim 11, wherein an insertion end of the pin is of a conical guide structure.

20. The air purifier housing according to claim 11, wherein the recessing openings are formed in opposite side walls of each said insertion groove; the number of the swing arms is two, and the two swing arms are symmetrically arranged; the second ends of the two swing arms are pivoted to the corresponding connecting rod, and the inner container protrusions at the first ends of the two swing arms correspond to the recessing openings in the opposite side walls of the corresponding insertion groove.

* * * * *